(12) United States Patent
Pors et al.

(10) Patent No.: US 7,963,176 B2
(45) Date of Patent: Jun. 21, 2011

(54) CLAMP-ON ULTRASONIC FLOW RATE MEASURING DEVICE HAVING A GUIDE FRAME FOR GUIDING THE ULTRASONIC TRANSDUCER

(75) Inventors: Jan Pors, Oud-Bijerland (NL); Jeroen v. d. Berg, Hendrik Ido Ambacht (NL); Marcel Molenaar, Oosterhout (NL); Jankees Hogendoorn, Spijk (NL)

(73) Assignee: Krohne AG, Basel (CH)

( * ) Notice: Subject to any disclaimer, the term of this patent is extended or adjusted under 35 U.S.C. 154(b) by 1089 days.

(21) Appl. No.: 11/694,196

(22) Filed: Mar. 30, 2007

(65) Prior Publication Data

US 2007/0232919 A1 Oct. 4, 2007

(30) Foreign Application Priority Data

Mar. 30, 2006 (DE) .......................... 10 2006 015 217

(51) Int. Cl.
*G01F 1/66* (2006.01)
(52) U.S. Cl. .................................. 73/861.28; 73/861.25
(58) Field of Classification Search .................. None
See application file for complete search history.

(56) References Cited

U.S. PATENT DOCUMENTS

| | | | | |
|---|---|---|---|---|
| 4,019,373 | A | * | 4/1977 | Freeman et al. ................ 73/644 |
| 4,425,803 | A | * | 1/1984 | Baumoel ..................... 73/861.18 |
| 4,454,767 | A | | 6/1984 | Shinkai et al. |
| 4,735,097 | A | * | 4/1988 | Lynnworth ................ 73/861.28 |
| 4,948,552 | A | | 8/1990 | Mollot et al. |
| 5,179,862 | A | * | 1/1993 | Lynnworth ................ 73/861.28 |
| 6,397,683 | B1 | | 6/2002 | Hagenmeyer et al. |
| 6,883,386 | B2 | | 4/2005 | Osone et al. |
| 7,500,402 | B2 | * | 3/2009 | Pors et al. ................... 73/861.28 |
| 2007/0107533 | A1 | * | 5/2007 | Molenaar et al. ............... 73/856 |
| 2007/0227264 | A1 | * | 10/2007 | Pors et al. ................... 73/861.28 |
| 2007/0232919 | A1 | * | 10/2007 | Pors et al. ..................... 600/454 |

* cited by examiner

*Primary Examiner* — Harshad Patel
(74) *Attorney, Agent, or Firm* — Roberts Mlotkowski Safran & Cole, P.C.; David S. Safran

(57) ABSTRACT

An ultrasonic flow rate measuring device, especially a clamp-on type, is mounted on a line through which medium flows with at least one ultrasonic transducer and a guide frame for guiding and holding the ultrasonic transducer. A fixing mechanism allows the ultrasonic transducer to be moved onto the line or away from the line and also allows it to be axially moved and fixed on the guide frame or unclamped from it. The ultrasonic flow rate measuring device is able to be easily unclamped for maintenance and repair purposes and then re-attachable to the line in the original configuration.

19 Claims, 5 Drawing Sheets

CLAMP-ON ULTRASONIC FLOW RATE MEASURING DEVICE HAVING A GUIDE FRAME FOR GUIDING THE ULTRASONIC TRANSDUCER

BACKGROUND OF THE INVENTION

1. Field of the Invention

The invention relates to an ultrasonic flow rate measuring device, especially a clamp-on ultrasonic flow rate measuring device, for measuring the flow rate through a line through which a medium flows, with at least one ultrasonic transducer and a guide frame for guiding and holding the ultrasonic transducer.

2. Description of Related Art

Clamp-on ultrasonic flow rate measuring devices are characterized in that they can be used especially easily. In contrast to other ultrasonic flow rate measuring devices that must be permanently integrated into the existing pipeline system by replacing a piece of the pipeline, clamp-on flow rate measuring devices can simply be placed from the outside on a suitable line section of the piping system. The line section to which the clamp-on ultrasonic flow rate measuring device is attached thus becomes a measuring line without the need for a separate measuring line that must be inserted into the piping system. This makes the use of clamp-on ultrasonic flow rate measuring devices simple and economical.

A problem with clamp-on ultrasonic flow rate measuring devices is obtaining the correct attachment of the measuring device to a line, especially with respect to the correct arrangement and alignment of the ultrasonic transducers, which in an ultrasonic flow rate measuring device are generally provided in spaced pairs located in the lengthwise direction of the line. Additionally, there is the problem that even a correctly positioned and aligned measuring device can become misaligned when the ultrasonic transducer must be removed from the line, for example for maintenance purposes.

Thus, there is a need for a simple and accurate mechanism for positioning and repositioning a clamp on flow rate measuring device.

SUMMARY OF THE INVENTION

An aspect of the invention is to provide an ultrasonic flow rate measuring device, especially a clamp-on ultrasonic flow rate measuring device, which after attachment to a line through which a medium flows can be easily unclamped for maintenance and repair purposes and then can be re-attached to the line in the original configuration.

In accordance with this invention, an ultrasonic flow rate measuring device is provided with a fixing mechanism by which the ultrasonic transducer, or sensor, can be moved toward the line or away from the line and can also be fixed on a guide frame or unclamped from it. The fixing mechanism assumes two functions. First, the transducer can be moved in a direction transverse to the line to position it on the line and finally pressed against it, in order to ensure good acoustic contact between the transducer and line. With this fixing mechanism, of course, the transducer can also be moved away from the line again so that it no longer makes contact with the line. Second, the fixing mechanism allows the transducer to be fixed on the guide frame and also for it to be unclamped again from it in order to move the axial position of the transducer with respect to the line.

According to a preferred embodiment of the invention, the ultrasonic flow rate measuring device can be attached to the line by means of a guide frame. In this connection, attachment can take place directly via the guide frame, or the guide frame can be movably attached, for example, to the fasteners that are attached to the line.

Further, the fixing mechanism can be made and arranged such that when the transducer is moved to engage the line, it is simultaneously fixed to the guide frame. Likewise, when the transducer is disengaged from the line, it is simultaneously unclamped from the guide frame.

In this discussion, unclamping the transducer from the guide frame means that the transducer remains attached to the guide frame, preferably captively, but is movable or slidable with respect to the guide frame. In particular, according to design, the transducer in the released state can be pushed or slid on the guide frame, preferably in its lengthwise direction, and in this way is guided by the guide frame. By this, the transducer can be slid within the guide frame while the frame is attached to the line to find the correct location for positioning the transducer. The transducer can then be fixed to that selected position on the guide frame, while at the same time being moved toward the line so that the transducer finally comes into contact with the line in order to achieve a good acoustic transition between the ultrasonic transducer and the line, and thus also to the medium flowing through the line.

The fixing mechanism can be accomplished in various ways in order to have the above described properties. According to a preferred embodiment of the invention, the fixing mechanism has a knob, which by its rotation in one direction, moves the ultrasonic transducer onto the line and at the same time fixes it on the guide frame. By turning the knob in the other direction, the ultrasonic transducer is moved away from the line and at the same time is released from the guide frame so that it may slide relative to the frame.

The fixing mechanism can fix the ultrasonic transducer on the guide frame by directly clamping the transducer to the frame or by a clamping mechanism provided on the ultrasonic transducer. Preferably in this connection, the fixing mechanism runs within a guide groove provided in the guide frame and clamps onto the walls of the guide frame that laterally border the groove to fix the ultrasonic transducer in position.

Fundamentally, the fixing mechanism interacts with the guide frame such that the ultrasonic transducer can be moved lengthwise in its unclamped or released state. In this case, for example, there can also be a groove or rail on the ultrasonic transducer or in a mechanism provided on the ultrasonic transducer; with the groove or rail extending as a corresponding counterpart to a portion of the guide frame.

As noted above, the guide frame with the ultrasonic transducer fixed on it can be unclamped from the line and afterwards re-attached to it. This means that the ultrasonic transducer also remains fixed in the guide frame in a predetermined manner when the guide frame is not attached to the line. This is especially important when there are two ultrasonic transducers that are each independently fixed at a predetermined distance from one another on the guide frame. In this state, the guide frame can be unclamped from the line and afterward re-attached to it while maintaining the relative positions of the transducers. This is especially an advantage after the initial correct alignment of the ultrasonic transducers is achieved since the configuration can be maintained even after repair or maintenance that requires that the ultrasonic transducers be removed from the line.

With clamp-on ultrasonic flow rate measuring devices, each ultrasonic transducer is provided with its own cable that connects it to the measurement electronics. This is a hindrance during the installation of a clamp-on ultrasonic flow rate measuring device, and also during removal and re-attachment of the clamp-on ultrasonic flow rate measuring device for maintenance or repair. Thus, in accordance with a preferred embodiment of the invention, an electrical connecting box is provided that has a connection for a cable to the ultrasonic transducer and a connection for a cable to the measuring device electronics.

Providing an electrical connecting box is advantageous in that the connecting box can be handled together with the guide frame and the ultrasonic transducer, for example while being removed from the line, without removing the cable from the ultrasonic transducer to the connecting box, while the cable is disconnected from the connecting box to the measuring device electronics.

The connections for a cable to the ultrasonic transducer or for a cable to the measuring device electronics can be made in different ways. According to a preferred embodiment of the invention, the connection for a cable to the ultrasonic transducer and/or for the connection for a cable to the measuring device electronics is provided as an independent plug-in connection.

It can be especially advantageous to run the cable to the ultrasonic transducer within the guide frame. In this way, there is essentially no risk that this cable will be adversely affected in the handling of the ultrasonic flow rate measuring device, for example when it is removed from the line.

Handling of the ultrasonic flow rate measuring device is especially simple when, according to another embodiment of the invention, the electrical connection box is attached to the guide frame.

Finally, according to another embodiment, two ultrasonic transducers can be provided each with a separate cable running to the connecting box, while there is only a single cable from the connecting box to the measuring device electronics. Thus, to disengage the ultrasonic flow rate measuring device from the line, only a single connection needs to be unclamped, specifically the connection of the cable from the measuring device electronics on the connecting box. This makes handling especially simple, and in particular specifically avoids having to handle more than a single cable.

The invention is explained in detail below with reference to the accompany drawings.

BRIEF DESCRIPTION OF THE DRAWINGS

FIG. 2a is a side perspective view partially cut away showing the ultrasonic flow rate measuring device of FIG. 1a;

Like reference numerals refer to like elements in the drawings.

DETAILED DESCRIPTION OF THE INVENTION

Figure 1A:
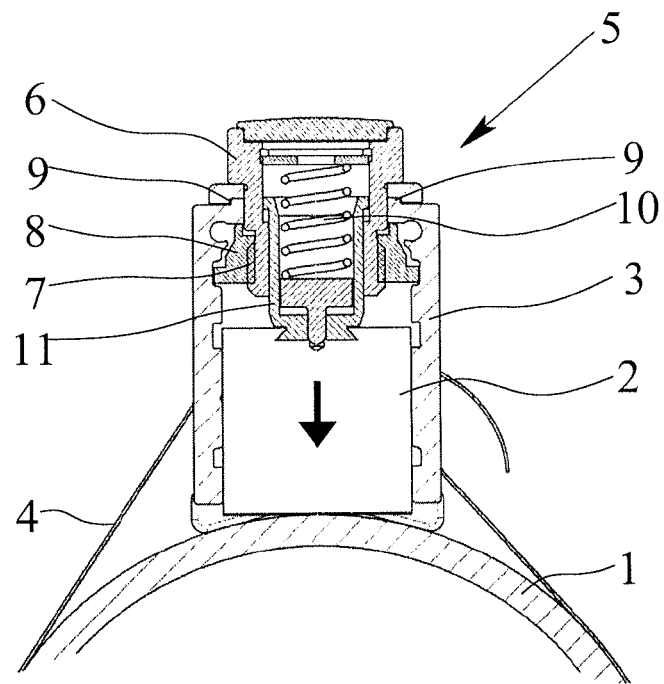
FIG. 1a is a side view in section of an ultrasonic flow rate measuring device connected to a line in a clamped, engaged state.
Figure 1B:
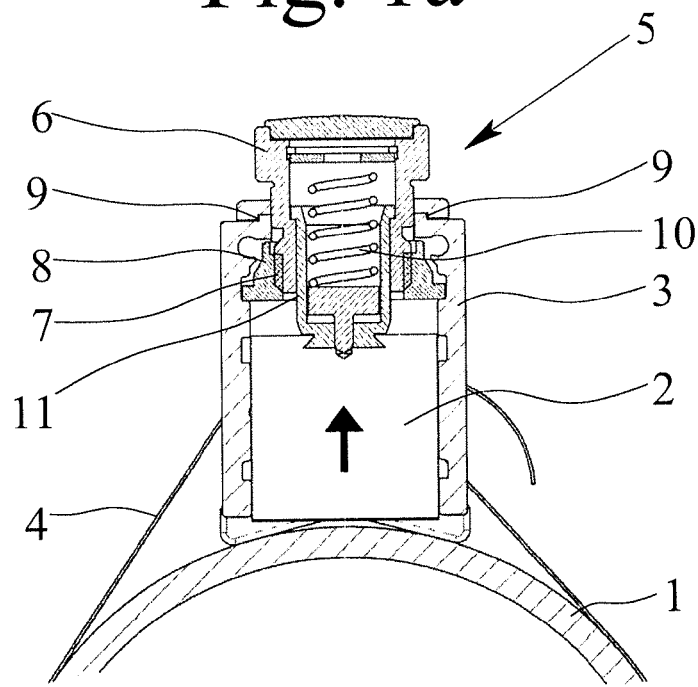
FIG. 1b is a side view in section of the ultrasonic flow rate measuring device of FIG. 1a in an unclamped, released state.

FIGS. 1a and 1b show a clamp-on ultrasonic flow rate measuring device in accordance with the invention mounted on a line 1 through which a medium can flow. The clamp-on ultrasonic flow rate measuring device includes an ultrasonic transducer 2 and a guide frame 3, which is used to guide and hold the ultrasonic transducer 2 and is attached by means of a fastening strap 4 to the line 1.

A fixing mechanism 5 is provided by means of which the ultrasonic transducer 2 can be moved perpendicularly to the lengthwise axis of the line 1 to be clamped onto the line, as seen by the arrow in FIG. 1a. Likewise, the ultrasonic transducer 2 can be released from the line by the fixing mechanism 5 causing it to move away from the line, as seen by the arrow in FIG. 1b. Simultaneously, the fixing mechanism 5 fixes the ultrasonic transducer 2 on the guide frame 3 when the ultrasonic transducer is moved toward the line 1. When the ultrasonic transducer 2 is moved away from the line 1, the ultrasonic transducer 2 is simultaneously unclamped from the guide frame 3. In this released state, the ultrasonic transducer 2 can then be moved parallel to the lengthwise axis of the line 1, therefore perpendicularly into or out of the plane of the drawings when viewing FIGS. 1a and 1b.

The fixing mechanism has a knob 6 that interacts via a thread 7 with a clamping mechanism 8 that is guided in the guide frame 3 parallel to the lengthwise axis of the line 1 by the interaction between grooves in the side walls of the guide frame 3 and complementary protrusions, such as rails, in the clamping mechanism 8. The top of the ultrasonic transducer 2 is attached to the knob 6. Turning the knob 6 clockwise or counterclockwise causes the ultrasonic transducer 2 to be pressed onto the line 1 or to be lifted away from line 1, respectively. The top of the knob 6 has a larger diameter than the middle part of the knob 6. By this as seen in FIG. 1a, the top part of the knob 6 rests on the side walls 9 of the guide frame 3, which border the groove running parallel to the lengthwise axis of the line 1 in the guide frame 3.

When the knob 6 is screwed clockwise into the clamping mechanism 8, the knob 6 presses down against the side walls 9 so that the clamping mechanism 8 is clamped at the top region of the knob 6, on the one hand, and is clamped below the side walls, on the other hand by the guide frame 3. Moreover, screwing the knob 6 into the clamping mechanism 8 moves the ultrasonic transducer 2 toward the line 1 so that the ultrasonic transducer 2 as a result presses securely on the line 1. This ensures a good acoustic transition. In this state, the ultrasonic transducer 2 can no longer move, especially not in the lengthwise direction of the guide frame 3.

To ensure high enough contact pressure for attaching the ultrasonic transducer 2 on the line 1 without risking damage to the ultrasonic transducer 2 by pressing onto the line 1, there is a spring 10 disposed within the knob 6. This spring 10 presses outwardly at one end against the top of the knob 6 and interacts at the other end with a spring housing 11, which can be moved in the knob 6 perpendicular to the lengthwise axis of the guide frame 3 and via which the ultrasonic transducer 2 is attached to the fixing mechanism 5.

Figure 2A:
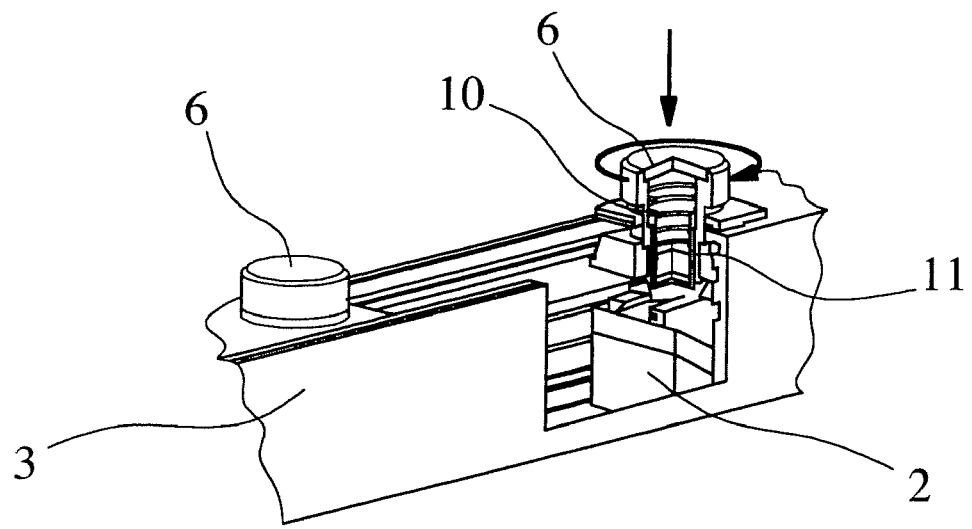
Figure 2B:
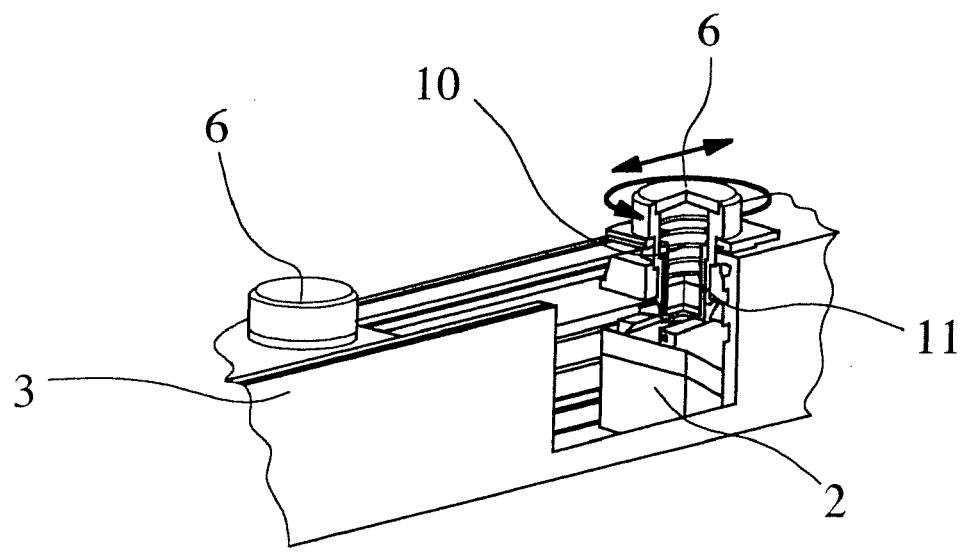
FIG. 2b is a side perspective view partially cut away showing the ultrasonic flow rate measuring device of FIG. 1b.

As is apparent from FIGS. 2a and 2b, turning of the knob 6 clockwise leads to fixing of the ultrasonic transducer 2 in the guide frame 3 such that movement of the ultrasonic transducer 2 in the lengthwise direction is no longer possible, this occurs while the ultrasonic transducer 2 is pressed securely onto the line 1. When the knob 6 is turned counterclockwise, the ultrasonic transducer 2 is raised off the line 1 and movement of the ultrasonic transducer 2 in the lengthwise direction of the guide frame 3 is possible, for example in order to axially re-position the ultrasonic transducer 2.

As is likewise apparent from FIGS. 2a and 2b, the clamp-on ultrasonic flow rate measuring device according to a first preferred embodiment of the invention described herein includes two ultrasonic transducers 2, with only the top part of the knob 6 of the left ultrasonic transducer being shown. For two ultrasonic transducers 2 of the clamp-on ultrasonic flow rate measuring device according to the invention, there is the advantage that after correct positioning of the ultrasonic transducers 2 they can be fixed on the guide frame 3. Then, the guide frame 3 can be removed from the line 1 without endangering the correct alignment of the ultrasonic transducers 2 with respect to one another.

As a result, a clamp-on ultrasonic flow rate measuring device is made available that can be easily unclamped from the line 1, for example for maintenance and repair purposes, without the ultrasonic transducers 2 having to be recalibrated to one another in a complex process upon re-attachment to the line 1.

Figure 3:
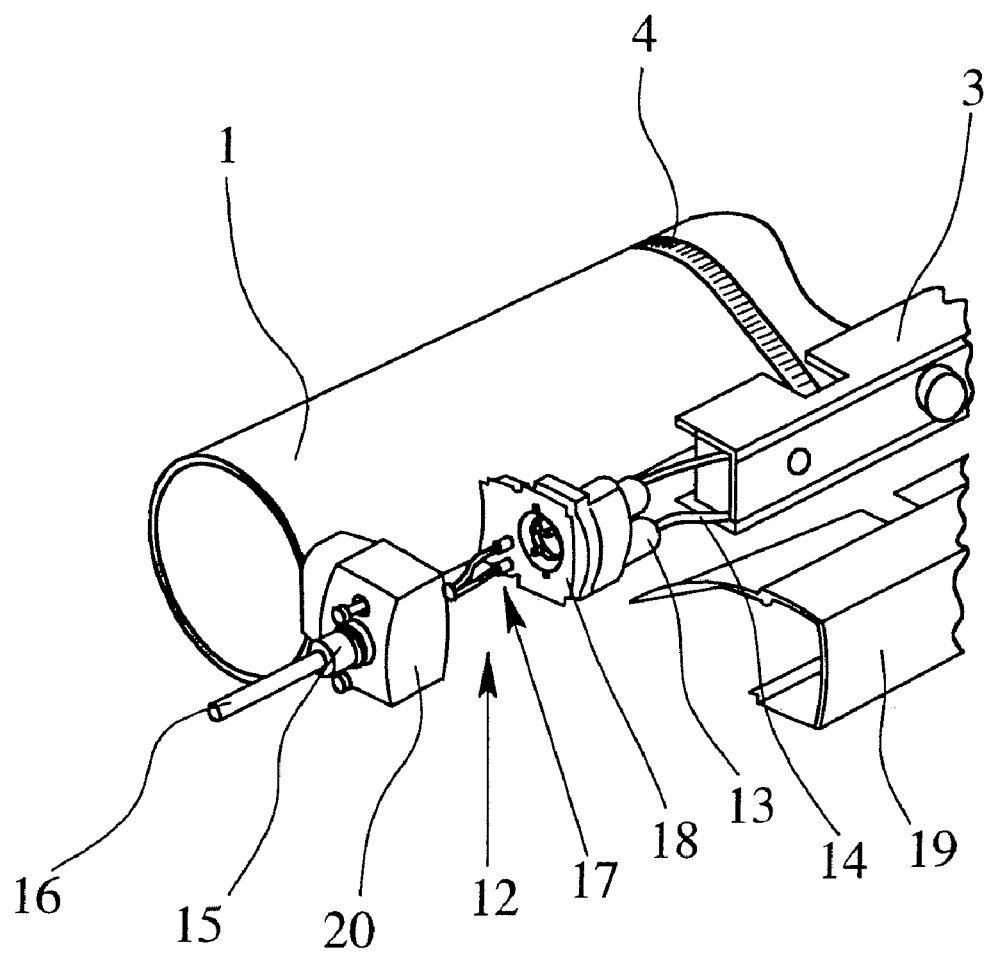
FIG. 3 is a side perspective exploded view of an ultrasonic flow rate measuring device in accordance with the invention including an electric connection box with the device mounted on a line.
Figure 4:
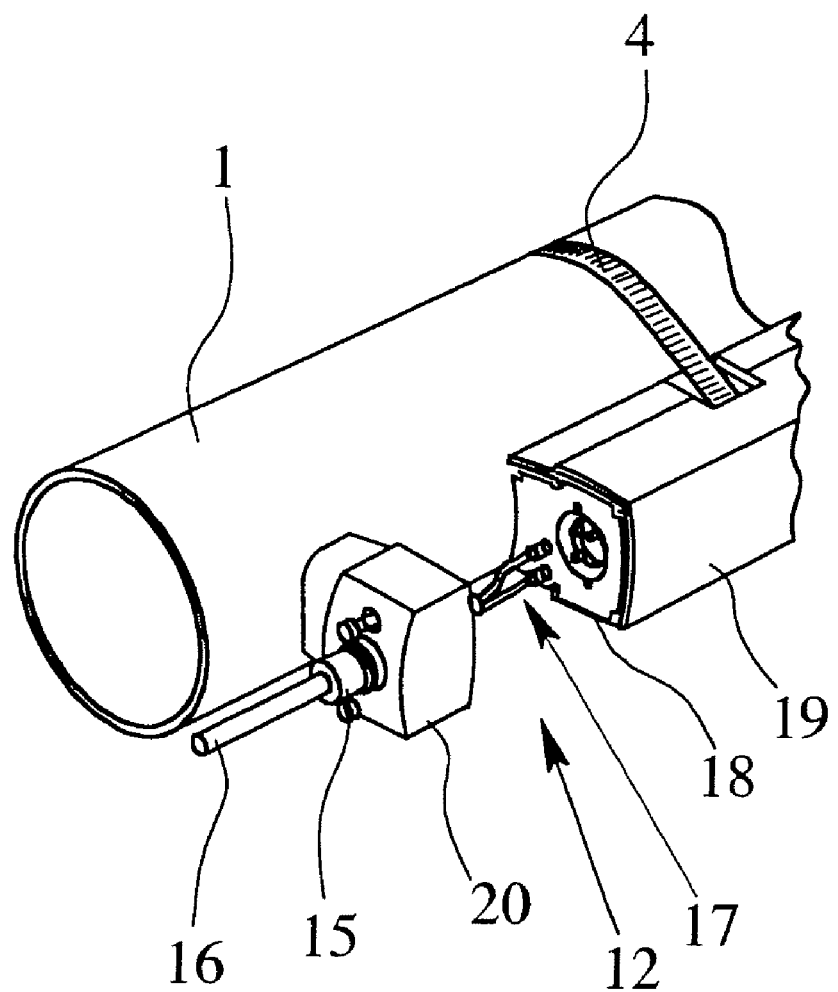
FIG. 4 is a side perspective view of an ultrasonic flow rate measuring device in accordance with the invention as shown in FIG. 3 partially assembled; and, FIG. 5 is a side perspective view of an ultrasonic flow rate measuring device in accordance with the invention as shown in FIG. 3 completely assembled.
Figure 5:
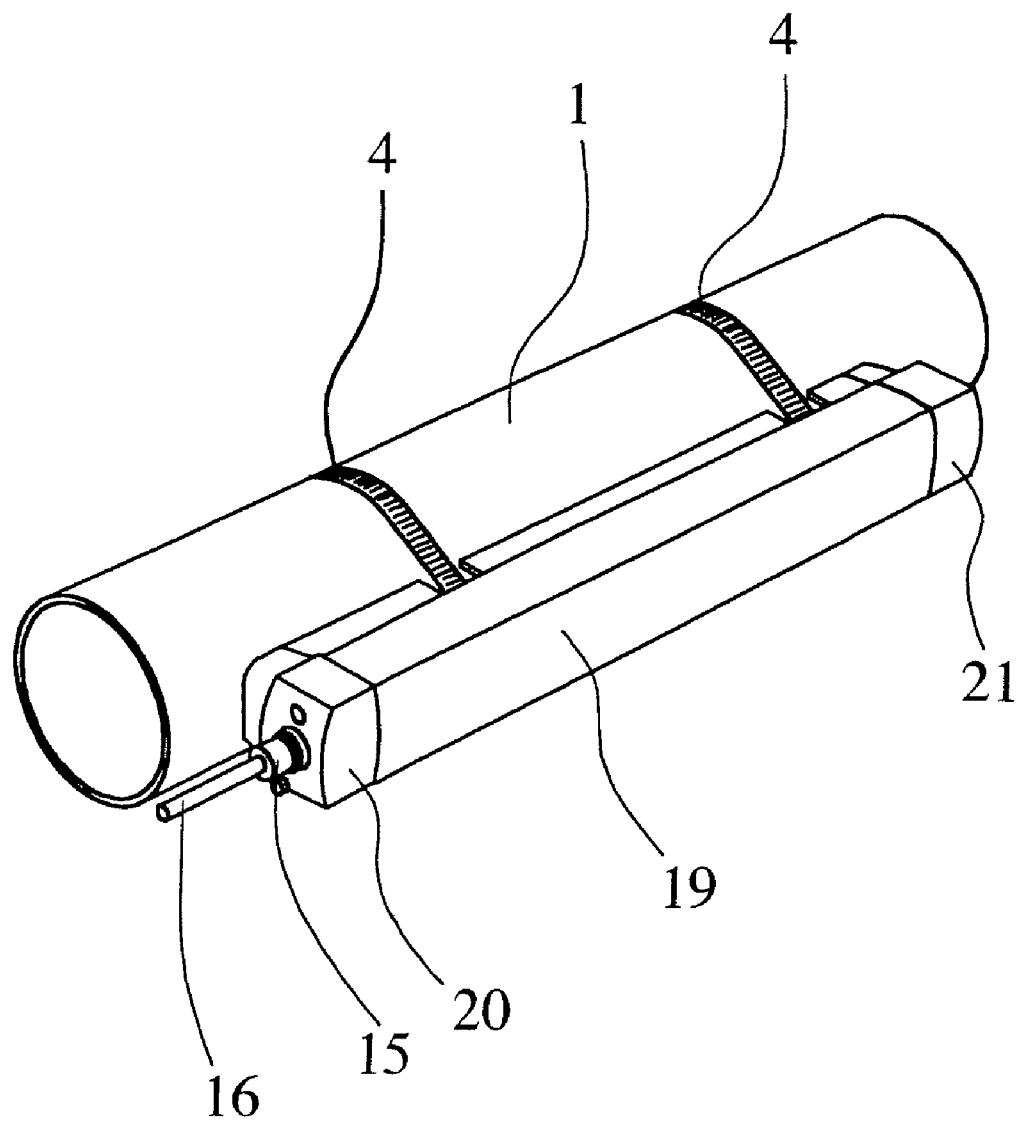

In the ultrasonic flow rate measuring device according the arrangement shown in FIGS. 3 to 5, essentially the same structure is provided as described above. In addition, however, an electrical connecting box 12 is provided. This electrical connecting box 12 has two connections 13, which lead via one cable 14 each to the ultrasonic transducers 2. Moreover, the electrical connecting box has a connection 15, which leads via a cable 16 to the measuring device electronics (not further shown.) The electrical connecting box 12 is made such that it has one plug-in connection 17, which can be easily unclamped in order to then be able to easily unclamp the entire assembly from the line 1.

As is especially apparent from FIGS. 3 and 4, the electrical connecting box 12 is made in two parts, the first part 18 being attached directly to the guide frame 3. When the ultrasonic flow rate measuring device is assembled, the device cover 19 is put in place before the second part 20 of the electrical connecting box 12 is attached laterally to the ultrasonic flow rate measuring device. The device cover is screwed to the first part 18 so that the device cover 19 is closed laterally. On the opposing side, the device cover 19 is closed by a corresponding cap 21 without a cable penetration.

Thus, an ultrasonic flow rate measuring device is achieved that is also easy to handle with respect to its cabling. Specifically, there is only little danger that when the ultrasonic flow rate measuring device is installed or removed from the line 1 one of the cables 13, 14, 16 will be damaged.

Modifications and changes can be made to the invention described herein and remain within the scope of the invention as described in the appended claims. For example, different types of sensors other than ultrasonic transducers can be used. Various materials can be used for the different components depending on the intended use. Further, the knob 6 can be configured for easy gripping or provided with a tool receiving formation to assist in turning. Various spring types or resilient materials could be used for the spring 10.

What is claimed is:

1. Ultrasonic flow rate measuring device for measuring a flow rate through a line through which a medium flows, comprising:
    at least one ultrasonic transducer;
    a guide frame for guiding and holding the ultrasonic transducer, the guide frame having a longitudinal axis; and,
    a fixing mechanism connected to the ultrasonic transducer to move the ultrasonic transducer in a direction perpendicular to the longitudinal axis toward or away from the line, and connected to the guide frame to move the ultrasonic transducer in a direction parallel to the longitudinal axis, and to selectively fix the ultrasonic transducer to the guide frame at a position and to selectively release the ultrasonic transducer from the position, wherein the fixing mechanism simultaneously fixes the ultrasonic transducer to the guide frame when moved toward the line and simultaneously releases the ultrasonic transducer from the guide frame when moved away from the line.

2. Ultrasonic flow rate measuring device as claimed in claim 1, wherein the guide frame includes an attachment device for attachment to the line.

3. Ultrasonic flow rate measuring device as claimed in claim 2, wherein the fixing mechanism includes a knob that is rotatable in a first direction to move the ultrasonic transducer toward the line while fixing it to the guide frame and rotatable in a second direction to move the ultrasonic transducer away from the line while releasing it from the guide frame.

4. Ultrasonic flow rate measuring device as claimed in claim 3, wherein the fixing mechanism includes a clamping element disposed within the guide frame that is threadably connected to the knob.

5. Ultrasonic flow rate measuring device as claimed in claim 4, wherein the knob is selectively rotatable to clamp the guide frame between the knob and the clamping element.

6. Ultrasonic flow rate measuring device as claimed in claim 3, wherein the knob is connected to the ultrasonic transducer via a spring.

7. Ultrasonic flow rate measuring device as claimed in claim 1, wherein the fixing mechanism clamps onto the guide frame to fix the ultrasonic transducer to the guide frame.

8. Ultrasonic flow rate measuring device as claimed in claim 1, wherein the ultrasonic transducer is slidable in the guide frame along its longitudinal axis when released by the fixing mechanism.

9. Ultrasonic flow rate measuring device as claimed in claim 8, the fixing mechanism includes a rail that interacts with the guide frame such that the ultrasonic transducer can be moved lengthwise in its released state.

10. Ultrasonic flow rate measuring device as claimed in claim 1, wherein the guide frame with the ultrasonic transducer fixed thereon is selectively attachable to the line.

11. Ultrasonic flow rate measuring device as claimed in claim 10, wherein two ultrasonic transducers are each fixed with a fixing mechanism on the guide frame at a predetermined distance from one another, wherein the guide frame with the two fixed ultrasonic transducers is selectively attachable to the line.

12. Ultrasonic flow rate measuring device as claimed in claim 1, further comprising an electrical connecting box including one electrical connection for a cable to the ultrasonic transducer and one electrical connection for a cable to measuring device electronics.

13. Ultrasonic flow rate measuring device as claimed in claim 12, wherein each electrical connection includes a plug-in connection.

14. Ultrasonic flow rate measuring device as claimed in claim 12, wherein the electrical connecting box is mounted to the guide frame.

15. Ultrasonic flow rate measuring device as claimed in claim 14, wherein the cable to the ultrasonic transducer runs within the guide frame.

16. Ultrasonic flow rate measuring device as claimed in claim 14, wherein there are two ultrasonic transducers disposed within the guide frame each with a cable and the electrical connecting box has an electrical connection for each ultrasonic transducer.

17. Ultrasonic flow rate measuring device as claimed in claim 12, further comprising a cover that connects to the electrical connecting box and surrounds the guide frame.

18. An ultrasonic flow rate measuring device for measuring flow of a medium through a line, comprising:

a guide frame for connection to a line to be measured and having side walls with interior grooves and a longitudinal axis;

at least one ultrasonic transducer mounted in the guide frame for movement parallel and perpendicular to the longitudinal axis; and a fixing mechanism that is connected to the ultrasonic transducer and includes a clamping element that slidably engages the interior grooves of the side walls of the guide frame and a rotatable knob that is rotatable to selectively clamp the side walls between the knob and the clamping element to fix the ultrasonic transducer with respect to the longitudinal axis while moving the ultrasonic transducer in a direction perpendicular to the longitudinal axis.

19. Ultrasonic flow rate measuring device as claimed in claim 18, further comprising an electrical connecting box mounted to the guide rail including a plug in connector for a cable to the ultrasonic transducer and a plug in connector for an external electrical component.

\* \* \* \* \*